(12) United States Patent
Yoshioka et al.

(10) Patent No.: US 7,540,184 B2
(45) Date of Patent: Jun. 2, 2009

(54) ANALYZING METHOD FOR COLORING MATERIAL COMPOSITION

(75) Inventors: Satomi Yoshioka, Suwa (JP); Shigeki Shimizu, Nagano-ken (JP)

(73) Assignee: Seiko Epson Corporation, Tokyo (JP)

( * ) Notice: Subject to any disclaimer, the term of this patent is extended or adjusted under 35 U.S.C. 154(b) by 575 days.

(21) Appl. No.: 11/304,495

(22) Filed: Dec. 15, 2005

(65) Prior Publication Data

US 2006/0150716 A1 Jul. 13, 2006

(30) Foreign Application Priority Data

Dec. 15, 2004 (JP) ............................. 2004-363629

(51) Int. Cl.
*G01N 30/00* (2006.01)
*G01N 30/90* (2006.01)

(52) U.S. Cl. .................. 73/61.55; 73/61.52; 73/61.54; 210/198.3; 210/658

(58) Field of Classification Search ............... 73/61.52, 73/61.54, 61.55; 210/198.2, 198.3, 656, 210/658
See application file for complete search history.

(56) References Cited

U.S. PATENT DOCUMENTS

| | | | | |
|---|---|---|---|---|
| 3,701,678 A | * | 10/1972 | Rossler et al. .............. 428/341 |
| 5,811,665 A | * | 9/1998 | Gregor et al. ............... 73/61.53 |
| 5,889,180 A | * | 3/1999 | Mc Culloch et al. ......... 536/127 |
| 6,420,181 B1 | * | 7/2002 | Novak .......................... 436/104 |
| 2007/0102635 A1 | * | 5/2007 | Ma et al. ................... 250/338.1 |

FOREIGN PATENT DOCUMENTS

| CN | 1258003 | | 6/2000 |
|---|---|---|---|
| JP | 2001-4612 | * | 1/2001 |
| JP | 2001-260381 | | 9/2001 |

OTHER PUBLICATIONS

English translation of CN 1258003 dated Jun. 28, 2007.
Patent Abstract of Japan and JPO Complete English Translation of JP 2001-260381 dated Sep. 25, 2001.

* cited by examiner

*Primary Examiner*—Daniel S Larkin
(74) *Attorney, Agent, or Firm*—Ladas and Parry LLP

(57) ABSTRACT

It is an object of the present invention to provide a method capable of easily identifying a coloring material composition. The method performs a chromatography step of loading a subject sample containing the coloring material composition to a chromatography apparatus that holds a separating base material containing a cellulosic material and a metallic oxide material, and of performing a chromatography using a mobile phase of a liquid in the analysis of the coloring material composition. According to such a chromatography apparatus, coloring materials contained in the coloring material composition can be favorably and easily separated.

9 Claims, 2 Drawing Sheets

Four-colors Ink    Six-colors Ink

ANALYZING METHOD FOR COLORING MATERIAL COMPOSITION

BACKGROUND OF THE INVENTION

1. Field of the Invention

The present invention relates to an analyzing method for a coloring material composition for easily identifying the coloring material composition, a chromatography apparatus for analyzing the coloring material composition, a chromatography kit for analyzing the coloring material composition, a failure diagnosing method for an image forming apparatus, and a system for diagnosing the failure of the image forming apparatus.

2. Description of the Prior Art

A coloring material composition, for example, an ink used for image forming apparatuses such as a printer adopting various recording methods such as an ink jet recording method and an electronic photograph recording method contains a specific dye and pigment so as to provide a high definition printing image. The ink often requires physical properties or the like corresponding to the printing properties of the printer simultaneously. Therefore, it is preferable to use an ink having properties corresponding to the printing properties of the printer so as to use the printer while maintaining a favorable condition, and suitable inks are often recommended by printer manufacturers according to the kind of printer.

For example, Japanese Published Unexamined Patent Application No. 2001-260381 (paragraph number "0003" or the like) discloses that various obstacles may be produced, for example, in an ink contact part in the printer such as an ink discharge part when the ink which is inconsistent with the ink properties required by the printer is used. Printed matter having sufficient quality of image may not be able to be printed. Therefore, it is also important to determine whether the used ink is suitable as soon as possible for the maintenance or repair of the printer causing the obstacle.

SUMMARY OF THE INVENTIION

However, an ink cartridge mounted to a failure machine may not be able to be obtained under various situations, and adequate information for the ink cartridge may not be able to be obtained. The ink used for the failure machine was not necessarily able to be confirmed immediately. Though the ink is extracted from a printed matter for which the quality of image was not secured, or a waste liquid tank, and the extracted ink can be analyzed by using instrumental analysis devices such as GC/MS, FT-IR and NMR, a lot of time has been required for obtaining the analysis results. So as to separate the coloring materials contained in the ink to the extent that the ink is identified by using a thin layer chromatography (TLC) and paper chromatography (PC) generally considered as a simple and quick analyzing method, it is necessary to select a developing liquid having a complicated composition. Also, spots are easily blurred in PC, and even distinction of the separated coloring material may be difficult. And in TLC, a solvent requiring attention for handling has been often used. Therefore, it has also been difficult to perform TLC and PC at a repair site to identify the ink.

An object of the present invention is to provide an analyzing method for a coloring material composition, a chromatography apparatus and a chromatography kit for analyzing the coloring material composition, which are capable of identifying the coloring material composition easily and promptly. Further, an object of the present invention to provide method and a system for diagnosing a failure of an image forming apparatus, which are capable of identifying the coloring material composition used for an image forming apparatus easily and promptly.

The present inventors have conducted earnest examinations to solve the above problem, and found that the coloring materials contained in the coloring material composition can be favorably separated by a chromatography using a separating base material obtained by combining a cellulosic material and a metallic oxide material beyond expectations. It has also been found that this chromatography can separate and identify the coloring materials promptly and clearly, and can identify a plurality of kinds of coloring materials easily. The present invention provides the following means.

The present invention is directed to an analyzing method for a coloring material composition, including a chromatography step of loading a subject sample containing the coloring material composition to a chromatography apparatus that holds a separating base material containing a cellulosic material and a metallic oxide material, and of performing a chromatography using a mobile phase of a liquid.

In the analyzing method of the invention, the separating base material may have a silica material and/or alumina material layer formed on the surface of the cellulosic material. In this case, the chromatography apparatus may be a thin layer chromatography apparatus, and the separating base material may have a silica material layer formed on the surface of the cellulosic material layer.

In the analyzing method of the invention, the solubility parameter of the mobile phase represented by the formula (1) may be within the range of 9.5 to 16.

Formula (1):

$$\text{Solubility Parameter of Mobile Phase } (d) = \sum_{i=1 \text{ to } n} (di \times Ri),$$

wherein i is one or more integers; di is the solubility parameter of the i-th solvent of n kinds of solvents constituting the mobile phase; Ri is the mixing ratio in the mobile phase of the i-th solvent of n kinds of solvents constituting the mobile phase; and the total from $R_1$ to $R_n$ is 1.

In the analyzing method of the invention, the mobile phase may be mainly composed of a polar solvent compatible with water.

The mobile phase may be mainly composed of ethanol. The mobile phase may be independently composed by ethanol.

In the analyzing method of the invention, the subject sample may be either of an extracted matter from an image forming apparatus containing the coloring material composition and an extracted matter from an image part formed on a recorded matter containing the coloring material composition.

The analyzing method of the invention may further include an identification step of identifying the coloring material composition contained in the subject sample based on the separating data of one kind or two kinds or more of coloring materials contained in the subject sample obtained by the chromatography step, and the separating data of the coloring material composition for analysis.

In the analyzing method of the invention, the coloring material composition may be an ink composition for ink jet. The coloring material may be a dye.

The present invention is also directed to a chromatography apparatus for analyzing a coloring material composition. The chromatography apparatus of the invention includes a separating base material containing a cellulosic material and a metallic oxide material in any one form of a column chromatography and a thin layer chromatography.

The present invention is also directed to a chromatography kit for analyzing a coloring material composition. The chromatography kit of the invention includes a thin layer chromatography apparatus that holds a separating base material containing a cellulosic material and a metallic oxide material, and a mobile phase applied to the thin layer chromatography apparatus containing ethanol, is provided.

The present invention is further directed to a failure diagnosing method for an image forming apparatus. The failure diagnosing method includes: a chromatography step of loading a subject sample containing a coloring material composition extracted from the image forming apparatus or a subject sample containing a coloring material composition extracted from a recorded matter outputted by the image forming apparatus to a chromatography apparatus that holds a separating base material containing a cellulosic material and a metallic oxide material and of performing a chromatography using a mobile phase of a liquid; and an identification step of identifying the coloring material composition contained in the subject sample based on the separating data of one kind or two kinds or more of coloring materials contained in the subject sample obtained by the chromatography step and the separating data of the coloring material composition for analysis.

The failure diagnosing method of the invention may further include a chromatogram information obtaining step of obtaining the chromatogram of the subject sample obtained by the chromatography step as digitalized chromatogram information prior to the identification step. Here, the identification step may identify the coloring material composition contained in the subject sample based on the chromatogram information obtained by the chromatogram information obtaining step and the separating data of the coloring material composition for analysis. The identification step may be executed by a computer.

The present invention is further directed to a system for diagnosing a failure of an image forming apparatus. The system for diagnosing a failure includes: an information controller controlling information for diagnosing the failure; and a failure information obtaining device obtaining failure information. The failure information obtaining device included in this system includes a chromatogram information obtaining module for loading a subject sample containing a coloring material composition extracted from the image forming apparatus or a subject sample containing a coloring material composition extracted from a recorded matter outputted by the image forming apparatus to a chromatography apparatus that holds a separating base material containing a cellulosic material and a metallic oxide material and for obtaining chromatogram obtained by performing a chromatography using a mobile phase of a liquid as digitized chromatogram information. The information controller includes an identifying module for identifying the coloring material composition contained in the subject sample based on the chromatogram information of the subject sample obtained from the failure information obtaining device and the separating data of the coloring material composition for analysis held by the information controller. The system for diagnosing the failure may further include a transmitting device for transmitting the chromatogram information of the subject sample to the information controller via a communications line.

DESCRIPTION OF THE PREFERRED EMBODIMENT

Figure 1:
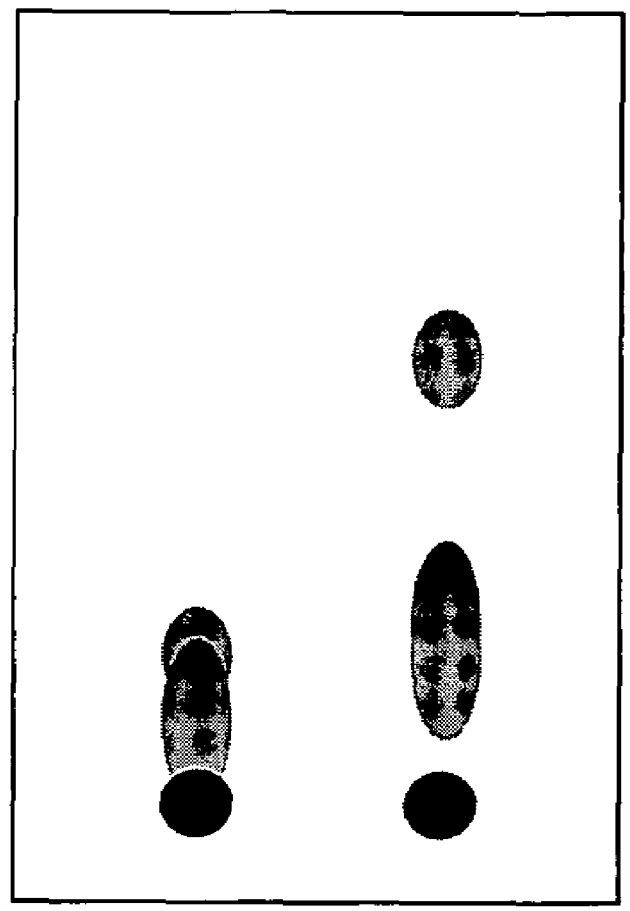
FIG. 1 shows an example of a chromatogram according to one embodiment.

The analyzing method for the coloring material composition for easily identifying the coloring material composition, the chromatography apparatus for analyzing the coloring material composition, the chromatography kit for analyzing the coloring material composition, the failure diagnosing method for the image forming apparatus, and the system for diagnosing the failure of the image forming apparatus according to the present invention relate to the chromatography step of loading the subject sample containing the coloring material composition to the chromatography apparatus that holds the separating base material containing the cellulosic material and the metallic oxide material and of performing the chromatography using the mobile phase of the liquid. Since the coloring materials contained in the coloring material composition such as ink can be separated with a favorable separation capacity beyond expectation according to this chromatography step, the coloring material composition can be easily and promptly identified. In particular, the coloring materials can be favorably separated by the mobile phase having a simple composition. Hereinafter, the description regards embodiments of the analyzing method for the coloring material composition, the chromatography apparatus, the chromatography kit, the failure diagnosing method for the image forming apparatus, and the system for diagnosing the failure according to the present invention.

Coloring Material Composition

The coloring materials of the present invention contain both a dye and a pigment. Examples of the dyes include various kinds of dyes such as a direct dye, an acid dye, a reactive dye and a basic dye. Examples of the pigments include various kinds of inorganic pigments and various kinds of organic pigments such as printing based pigments, azo based pigments and phthalocyanine pigments. Although the organic pigment may be a lake pigment and a toner pigment, the lake pigment is more suitable for the analyzing method of the present invention.

The coloring material composition is not particularly limited as long as the coloring material composition contains the dye and/or the pigment as the coloring material. Examples of the coloring material compositions include the ink and toner for various kinds of image forming apparatuses. Examples of the image forming apparatuses include a printer, a facsimile, a copy machine and a compound machine obtained by compounding two or more kinds of these devices. Examples of image recording methods in the image forming apparatus include an electronic photograph method using a laser beam or the like in addition to an ink jet recording method. It is preferable that the ink is a water-based ink using water and/or an organic solvent soluble in the water as a medium. The coloring material in these water-based inks may be only the dye, and may be obtained by combining the dye and the pigment. Also, the coloring material may contain only the pigment as the coloring material. Since the dye and pigment for ink jet can be favorably separated, the ink for ink jet recording method, particularly the water-based ink is preferable as the coloring material composition of the present invention. The toner using the pigment and the dye is also preferable as the coloring material composition of the present invention.

Subject Sample

The subject sample according to the analyzing method of the present invention contains the coloring material composition. The subject sample according to the present invention can adopt various aspects. For example, the subject sample may be an extracted matter from the image forming apparatus containing the coloring material composition, and an extracted matter from an image part on a recorded matter containing the coloring material composition. The ink or toner (hereinafter, referred to as ink or the like) for the image forming apparatus such as the printer is illustrated below. The ink or the like may not be necessarily a product itself, and may be an ink as an adhered matter extracted from an adhered part of the ink or the like in the printer, and a waste ink extracted from a storage part of the ink or the like in the printer in addition to a bottle ink before filling a cartridges of the ink or the like and an ink extracted from an ink cartridge attached to the printer or collected. Examples of the adhered parts of the ink or the like include a supply route for the ink or the like such as a head part of the printer and a cap part of a head. Examples of the storage parts of the ink or the like include a waste liquid pad and waste liquid tank for disposal or redundant ink or the like. The subject sample may be an ink or the like extracted from an image forming part on the recorded matter.

When the ink or the like is extracted from these parts and the ink or the like is a liquid, the ink or the like can be used as it is as the subject sample, or can be used as the subject sample by suitably diluting or condensing the ink or the like. When the extracted ink or the like is a solid by drying or the like, or is a solid such as powder or the like, the ink or the like can be used as the subject sample by dissolving it in a suitable solvent, or extracting it after extracting it as the solid. Regardless of being a liquid or a solid, a cleaning liquid obtained by washing the adhered part or the like by the suitable solvent can be used as the subject sample as it is. Or the cleaning liquid can be used as the subject sample by suitably concentrating, diluting and extracting. When the coloring material composition is the liquid such as the ink for ink jet, the extracted ink can be used as the subject sample as it is. Although particularly the conventional coloring material such as the dye and pigment used for the ink for ink jet such as the water-based ink for ink jet has poor separation due to TLC and PC, the chromatography of the present invention can separate the coloring material favorably. The subject sample may be extracted by adhering just only the ink or the like to the tip of a swab, and the subject sample of the required amount can be easily extracted.

The subject sample may be the mixture of the above various coloring material compositions in addition to the various coloring material compositions as long as the subject sample contains the coloring material composition. For example, two or more kinds of inks used in the printer are adhered to the adhered part of the ink or the like of the printer, and the used ink is collectively stored in the storage part such as the waste ink. Therefore, each color ink and ink of the same color and different kind are mixed in these parts. The ink on the recorded matter is also usually extracted as the mixture of each color ink. Examples of the mixtures of two or more kinds of coloring material compositions include the mixture of two or more kinds of inks manufactured by different manufacturers such as the mixture of genuine ink and non-genuine ink.

Other examples of the coloring material compositions include a food additive and a colored food itself.

Separating Base Material

The separating base material containing the cellulosic material and the metallic oxide material is used for the chromatography used for the present invention. An artificial cellulose and various derivatives obtained by introducing a functional group such as an acetyl group and an alkyl group into hydroxyl groups of the cellulose can be used for the cellulosic material in addition to a natural cellulose separated from a lignocellulosic material. The cellulosic material is preferably combined with the metallic oxide material in any of a laminated shape such as a sheet shape, a granular shape, a fibrous shape or a powdery shape or the like.

Examples of the metallic oxide materials include various compounds having a metasiloxane bond such as silica ($SiO_2$) and alumina ($Al_2O_3$). Metal species constituting the metasiloxane bond contained in the metallic oxide material may be two or more kinds such as Si and Al. One obtained by introducing an organic group into a main chain and side chain of a metalloxane frame can be suitably used for the metallic oxide material. The organic group may be an amino group, a cyano group and a carboxyl group or the like in addition to a hydrocarbon group such as an alkyl group. It is preferable that the metallic oxide material contains silica. The metallic oxide material is preferably combined with the cellulosic material in the aspect of the laminated shape or powdery shape.

Without particularly limiting each form of the cellulosic material and metallic oxide material, and the compound form thereof, the separating base material can be constituted in various kinds of forms. At least a part of the surface of the cellulosic material may have a metallic oxide material layer. In this case, the cellulosic material layer may be formed on a support such as glass and plastic, and the metallic oxide material layer may be formed on at least a part of the surface. At least a part of the surface of the metallic oxide material may have the cellulosic material. Furthermore, a matrix may be formed by the cellulosic material and the metallic oxide material. Both the cellulosic material and the metallic oxide material are preferably a porous material.

It is preferable that the surface side of the separating base material coming into contact with the subject sample has the metallic oxide material, since the metallic oxide material such as silica can adsorb the coloring material such as the dye sufficiently to prevent the diffusion effectively. The existence of the cellulosic material at the surface side is not completely eliminated, and the existence of the metal oxide material at the back surface or inner side of the separating base material is not eliminated.

The separating base material may contain a binder for combining the cellulosic material with the metallic oxide material. Examples of the binders include a soluble or water dispersible resin such as polyvinyl alcohol, polyvinylpyrrolidone, a soluble acrylic resin and a vinyl acetate-ethylene emulsion. The separating base material may contain a fluorescer. The separating base material can contain a basic compound such as amine and polyamine and a polyvalent metallic salt according to the coloring material for analysis. Thus, the separation capacity of the coloring material due to the separating base material can be adjusted.

The separating base material can be obtained by applying a general producing method of a thin layer in a filler of a liquid chromatography and a thin layer chromatography. The metallic oxide material can be obtained by a sol-gel method, and the hydrolysis and polycondensation or the like of an organic metallic compound such as alkoxysilane.

The following is the reasoning, and does not restrain the present invention. It is considered that the separating base material having the combination of the metallic oxide material and the cellulosic material separates the coloring material favorably using (1) the moderate control of the diffusion of the coloring material at the time of the load of the subject sample and the application of the mobile phase, (2) the distribution to the coloring material contained in the coloring material composition and the cellulosic material and/or metal oxide material of the other solvent ingredients, in particular, the adsorption of the coloring material to the metallic oxide material and the adsorption or the like of the solvent ingredients or the like to the cellulosic material. Also, it is considered that the favorable separation is also obtained by the simple mobile phase composition. It is further considered that the separation ratio of the coloring material is enhanced by using the mobile phase mainly composed of the high polar solvent which is not usually used for polar adsorbent such as silica and alumina to the separating base material.

Chromatography Apparatus

The form of the chromatography apparatus is different according to the compound form of the cellulosic material and metallic oxide material. Either a form (column chromatography apparatus) where a suitable column is filled up with the separating base material such as the powdery shape and the granular shape or a form (thin layer chromatography apparatus) where the separating base material is formed into a thin layer is preferable. In the case of the column form, a suitable column can be filled up with one in which the metalloxane material layer or the cellulosic material layer is formed on the surface of a cellulosic or metallic oxide material particle. In the case of the thin layer form, the thin layer can be obtained by forming the metal oxide or cellulosic material layer on the surface of the cellulosic or metallic oxide material layer. In a preferable form, the surface of the cellulosic material layer has the silica material layer. In the case of the thin layer form, a sheet body or the like for filter can be used as the cellulosic material layer. So as to support the cellulosic material layer and the metallic oxide material layer, a support body of the material such as glass, plastic and aluminum can also be separately used.

In the case of the thin layer chromatography apparatus, it is preferable that the loaded part of the subject sample on which the subject sample is loaded is previously provided on a predetermined part. Specifically, the part on which the subject sample is loaded and the size thereof can be marked. Thus, the accuracy of identification of the coloring material composition can be secured. Although the form of the loaded part of the subject sample may be spot-like and may be streak-like, the spot-like form is preferable.

Mobile Phase

Although the mobile phase can be arbitrarily set according to the form of subject sample and the coloring material composition for analysis, it is preferable that the mobile phase contains the organic solvent (hereinafter, referred to as high polar solvent) compatible with water. By containing the high polar solvent, the coloring materials can be favorably and promptly separated by the separating base material according to the present invention. Further, a favorable degree in separation can be secured for the coloring material having solubility or resolvability or dispersibility to the organic solvent compatible with water. Furthermore, the volatility of the mobile phase is suppressed by containing the high polar solvent, and the chromatogram excellent in reappearance ratio is obtained. Although such a high polar solvent can also constitute the mobile phase independently, the mobile phase can also be constituted by combining two or more kinds of high polar solvents. Herein, "mixing ratio" is based on the rate of the volume of each solvent used for constituting the mobile phase unless otherwise noted.

Examples of the high polar solvents include linear or branched alcohols having 1 to 5 carbon atoms such as methanol, ethanol, n-propanol, 2-propanol, n-butanol, sec-butanol and tert-butanol; glycols such as an alkylene glycol having 2 to 4 carbon atoms such as ethylene glycol, propylene glycol and butylene glycol and polyethylene glycols having 2 to 4 carbon atoms such as triethylene glycol and diethylene glycol; 1,2-diols such as 1,2-pentanediol, 1,2-hexanediol and 1,2-heptanediol; ketones, such as acetone, methyl ethyl ketone and diethyl ketone; an oxygen containing a saturated hydrocarbon ring compound such as tetrahydrofuran (THF); glycol monoalkyl ethers such as diethylene glycol monomethyl ether, diethylene glycol monoethyl ether, diethylene glycol monopropyl ether, diethylene glycol monobutyl ether, propylene glycol monomethyl ether, propylene glycol monoethyl ether and propylene glycol monobutyl ether; and amines such as triethyl amine and trimethyl amine.

The alcohols are preferably methanol, ethanol and 2-propanol, and more preferably ethanol. The ethanol is an excellent mobile phase even independently, and a favorable mobile phase can be constituted by combining the ethanol with one kind or two kinds or more selected from methanol, acetone, THF, 1,2-hexanediol, 2-propanol and hexane. Particularly, the methanol and/or acetone for which the solubility parameters are adjacent with each other are preferable as a combined use solvent. The methanol is a favorable mobile phase even independently. However, even when the methanol is used by combining the methanol with one kind or two kinds or more selected from acetone, THF, 1,2-hexanediol and chloroform, a favorable mobile phase can be constituted. It is particularly preferable to use acetone and/or 1,2-hexanediol as the combined use solvent. It is preferable that 2-propanol constitutes the mobile phase with acetone and/or 1,2-hexanediol.

Polyalkylene glycols are preferably triethylene glycol, and the ketones are preferably acetone. The oxygen containing a saturated hydrocarbon ring compound is preferably tetrahydrofuran. 1,2-diols are preferably 1,2-hexanediol and 1,2-pentanediol, and more preferably 1,2-pentanediol.

It is preferable that the mobile phase contains polyalkylene glycols such as triethylene glycol and 1,2-diols such as 1,2-hexanediol at the mixing ratio of 10 v/v % or less since these solvents are effective in small quantities for controlling the polarity of the mobile phase. The mixing ratio is more preferably 5 v/v % or less.

The mobile phase can contain water. The contained water can suppress the volatility of the mobile phase. The contained water can enhance the polarity of the mobile phase. When the content of water is too much, the separation capacity tends to be reduced. Therefore, although the preferable content of water is different according to the combination with the high polar solvent used together, for example, it is preferable that the mixing ratio of water to ethanol is 20 v/v % or less, and more preferably 10 v/v % or less, and still more preferably 5 v/v % or less when the mobile phase is constituted by ethanol and water.

The mobile phase can contain a nonpolar solvent incompatible with water. Examples of the nonpolar solvents include chloroform, dichloromethane, xylene and hexane. Even when only the nonpolar solvent is used as the mobile phase in the present invention, a favorable separation is hardly obtained.

A water-soluble organic solvent which may be used for the coloring material composition such as ink can also be used for the mobile phase. For example, the organic solvent which may be used as a moistening agent and a penetrating agent or the like can be used for the mobile phase.

The mobile phase suitable for the separation of the coloring material can also be selected by the solubility parameter (d) calculated by the following formula (1). In the chromatography of the present invention, the coloring materials can be effectively separated by setting the solubility parameter of the mobile phase according to the kind of subject sample and the kind of coloring material composition for analysis. For example, the solubility parameter for the coloring material (dye or the like) such as the ink for ink jet is preferably 9.5 to 16. In this range, the coloring materials can be favorably and promptly separated by using the separating base material according to the present invention. The solubility parameter is more preferably 11 or more, and still more preferably 12 or more. When the solubility parameter is 11 or more, the coloring materials can be favorably separated. When the solubility parameter is 12 or more, a more excellent separation capacity is shown. The solubility parameter is more preferably 15 or less, and still more preferably 14 or less. Therefore, the solubility parameter is more preferably within the range of 11 to 15, and is also more preferably within the range of 11 to 14. It is still more preferably with in the range of 12 to 14. Table 1 illustrates the solubility parameters (d) of typical solvents.

$$\text{Solubility Parameter of Mobile Phase } (d) = \sum_{i=1\,to\,n} (di \times Ri), \quad \text{Formula (1)}$$

wherein i is one or more integers; di is the solubility parameter of the i-th solvent of n kinds of solvents constituting the mobile phase; Ri is the mixing ratio in the mobile phase of the i-th solvent of n kinds of solvents constituting the mobile phase; and the total from $R_1$ to $R_n$ is 1.

Herein, the solubility parameter of each solvent is based on the description of "size exclusion chromatography" (by Sadao Mori, Kyoritsu Shuppan (1991)).

TABLE 1

| Solvent | Solubility Parameter (d) |
|---|---|
| Hexane | 7.3 |
| THF | 9.1 |
| Chloroform | 9.3 |
| Acetone | 9.9 |
| Ethanol | 12.7 |
| Methanol | 14.5 |
| Water | 23.4 |

As shown in Table 1, preferable examples of the high polar solvents for independently constituting the mobile phase include ethanol (d: 12.7). It has been found that the high polar solvent having the solvent parameter of 11 to 14 independently can constitute the mobile phase in a single solvent. Since changes by each worker and daily composition ratio are avoided, and no impurities are mixed in the mobile phase consisting of such a single solvent, a reproducible chromatogram is easily obtained. Therefore, the strictness and accuracy of the analysis results are improved. Examples of the high polar solvents include dimethyl formamide and dimethyl sulfoxide. When the mobile phase is constituted by a mixed solvent of a plurality of solvents, the reproducible chromatogram can be obtained by adjusting volatility. The ethanol is also preferable in view of easy handling.

It has been found that acetone (d: 9.9) and methanol (d: 14.5) in addition to the ethanol are a preferable solvent for use by combining two or more kinds from these, and are a preferable solvent for adjusting the solubility parameter by combining these with other high polar solvents.

As described above, Table 2 can illustrate examples of the preferable mobile phases (the mixture ratio is based on the volume of each solvent).

TABLE 2

| Composition of Mobile Phase |
|---|
| Ethanol |
| Methanol |
| Methanol•Ethanol (1:4) |
| Ethanol•Water (100:1 to 100:15) |
| Acetone:Methanol (3:2 to 4:1) |
| Acetone•Ethanol (1:1) |
| Acetone•Ethanol•Methanol (2:2:1) |
| Acetone•Methanol•THF•1,2-HD (20:10:1:1) |
| Chloroform•Methanol (1:5) |
| THF•Methanol (1:1) |
| Hexane•Ethanol•Methanol (2:1:3) |
| Acetone |
| Acetone•TEG (20:1) |
| Acetone•2-propanol (20:0.2) |
| Acetone•Methanol•1,2-HD (20:10:1) |
| Acetone•2-propanol•1,2-HD (20:0.2:1) |
| Acetone•2-propanol•1,2-HD•Methanol (20:0.2:1:10) |
| THF•water (10:1) |

THF: Tetrahydrofuran
1,2-HD: 1,2-hexanediol
TEG: Triethylene glycol

Load of Subject Sample

The subject sample is loaded to a suitable part of the separating base material. When the separating base material adopts the form of the thin layer chromatography, the subject sample of the proper amount is spotted to the suitable part of the base material, and the spot is dried if needed. The diffusion of the coloring material is suppressed by drying, and the chromatogram showing sharp separation is easily obtained. When the separating base material adopts the form of the column chromatography, the subject sample is loaded to the sample introduction side of the column by a suitable method.

Chromatography Step

The conditions of the chromatography step are selected according to the form of the separating base material. It is preferable that the present invention having a simple structure where the chromatography step in the form of the thin layer chromatography can be executed can separate the coloring materials, and can easily identify the coloring materials. When the chromatography step is executed in the form of the thin layer chromatography, after the mobile phase (developing solvent) is filled up in the chamber and is saturated, the separating base material to which the subject sample is loaded is set in the chamber. The mobile phase is developed to the suitable part to separate the coloring materials, and the separating base material can be taken out from the chamber to dry the separating base material. A preferable separation tends to be obtained at a developing temperature of about 38° C. to about 42° C. For example, when ethanol is independently used as the developing solvent, a preferable separation is obtained at not around 25° C. but around 40° C. It is preferable to use a solvent having a grade of higher purity referring to moisture or metal ions as the developing solvent.

When the thin layer chromatography step is executed, it is preferable that each coloring material contained in the coloring material composition for analysis or the coloring material composition thereof is simultaneously loaded by the same chromatography apparatus and is separated. The coloring material composition for analysis may be loaded by mixing two or more kinds of coloring materials, or may be loaded for every coloring material. So as to secure the strictness and accuracy of the separation, it is preferable to develop a standard substance having a known Rf value simultaneously with the subject sample to confirm the Rf value. It is preferable to use the coloring material for the standard substance.

When the chromatography step is executed in the form of the column chromatography, the mobile phase is flown, and the coloring materials are separated in the column. The coloring materials may be finally eluted from the column and detected as peaks by a suitable detector, or may be held in a condition where the coloring materials are separated in the column. Since the coloring materials have their own color, when a transparent column is filled up with the separating base material of white to light color, the separation form of the coloring materials can be visually recognized from the outside as the chromatogram by holding the coloring materials by being separated in the column. So as to secure the strictness and accuracy of the separation in the column chromatography, it is preferable to load the standard substance to the column simultaneously with the subject sample to confirm the retention time (RT) of the standard substance.

One kind or two kinds or more of the coloring materials contained in the subject sample are favorably separated according to the chromatography step. The coloring materials may be three or more kinds, and the coloring materials of about ten kinds are easily separated.

Identification Step

After the chromatography step is executed in this way, the coloring material composition contained in the subject sample is identified from the obtained chromatogram based on the separating data of one kind or two kinds or more of coloring materials contained in the subject sample, that is, the chromatogram, and the spot and the color tone (may be based on the absorption spectrum of the peak in the case of the column chromatography) of a band in the chromatogram, and Rf value or RT. The identification is to determine whether the coloring material composition contained in the subject sample is consistent with the coloring material composition for analysis. Specifically, in the identification step, the chromatogram (containing the separating data, the same applies hereinafter) of the subject sample is contrasted with the chromatogram obtained by simultaneously separating the known chromatogram of the coloring materials contained in the coloring material composition for analysis or the coloring material composition for analysis. Whether both chromatograms are recognized as the same coloring material composition from the whole of each chromatogram, or are recognized as the same coloring material composition from the separating data of each separated spot or band or the like on each chromatogram is determined. When contrasting with known separating data without executing the chromatography step of the coloring material composition for analysis simultaneously, the separating data of the subject sample may be corrected by the separating data of the standard substance.

Since the coloring materials are favorably separated by the chromatography step in the identification step, whether the coloring materials for analysis are contained or not can be easily and clearly identified by the chromatogram itself and the separating data obtained from the chromatogram. Therefore, regardless of an operator's identifying capability, the coloring material composition can be easily identified in a short time. When the subject sample contains at least one kind of the coloring material which is not contained in the coloring material composition for analysis, or does not contain the coloring material contained in the coloring material composition for analysis, the identification step can determine that the coloring material composition contained in the subject sample is inconsistent with the coloring material composition for analysis. In the case of the former, it can be determined that the coloring material composition contained in the subject sample is different from the coloring material composition for analysis, or contains additional coloring materials even if the coloring material composition contained in the subject sample contains the coloring material composition for analysis. In the case of the latter, it can be determined that the coloring material composition contained in the subject sample does not contain the coloring material composition for analysis.

Since two or more kinds of coloring materials can be favorably separated in the chromatography step in the identification step, the coloring material composition containing two or more kinds of coloring materials can be easily identified. For example, even when the coloring material composition containing the ink or toner for color printing such as cyan, magenta, yellow and black is used as the subject sample, the coloring material composition can be easily identified. The coloring materials of the spot or the like can be collected from the chromatogram if needed, and thereby the coloring materials can also be further analyzed.

In particular, when the chromatography step is executed in the form of the thin layer chromatography, the color tone and Rf value can be easily grasped by visual observation without using a special detection means from the chromatogram, and the color tone and Rf value can be identified from the coloring material composition for analysis by only the view of the chromatogram in many cases. Since the thin layer chromatography can execute the chromatography step with the simple composition, the chromatography step can be executed at that place where the subject sample is extracted, and can also identify at that place. Since in particular, the chromatography step has favorable separation, the identification can be completed at an early stage in a short developing time.

Before contrasting the separating data obtained from the subject sample with the separating data for analysis, the identification step can execute a chromatogram information obtaining step obtaining as chromatogram information obtained by digitizing the information of the chromatogram of the subject sample. In contrast, the separating data such as the Rf value may be read by reading the digitized chromatogram information into the computer, and displaying the information on a display, and the separating data can also be read by using an image-analysis software if needed. The computer can extract the separating data from the chromatogram by digitizing the chromatogram of the subject sample to obtain the information, and it is convenient for preservation. When the separating data thus obtained is contrasted with the separating data for analysis, and the separating data for analysis is previously stored in the computer or a suitable storage medium, a series of steps for contrasting the separating data of the subject sample with the separating data for analysis can also be performed by the computer. So as to digitize the subject sample and the chromatogram for analysis to obtain the information, an image information obtaining device of a CCD method such as a scanner and a digital camera can be used.

The identification step may be performed in an information controller such as a server and computer connected via the communications line, or in a separate terminal connected to the information controller. According to such a form, even when the chromatogram of the subject sample is obtained, the identification step can be easily executed under unified determining standard. Specifically, for example, when the chromatography step is performed and the chromatogram of the subject sample is obtained, the chromatogram is obtained by the image information obtaining device such as the scanner and the digital camera. The obtained chromatogram information is transmitted to the information controller which is in a remote place via the communications line. Thereby, the coloring material composition of the subject sample can be identified by contrasting the chromatogram information with the separating data for analysis in the information controller. The determination result in the information controller can also be transmitted via the communications line from the information controller to the receiving device which is in an execution place in the chromatography step. Thus, even when the separating data for analysis is not held in the execution place of the chromatography step, or even when the determination is difficult, the coloring material composition can be easily identified if the chromatogram of the subject sample exists. Although the identification step may be executed by the server and the computer, the identification can be handled by an identifying person.

The chromatography step and identification step described above are also useful in the failure diagnosing method for the image forming apparatus such as the printer, and these various steps can constitute the failure diagnosing method for the image forming apparatus. The failure diagnosing method for the image forming apparatus can also be provided with the chromatogram information obtaining step performed prior to the identification step, a chromatogram information transmitting/receiving step and a determination result transmitting/receiving step.

The device for executing each step in the failure diagnosing method for the image forming apparatus is also useful as the system for diagnosing the failure of the image forming apparatus, and the device for executing each step can constitute the system for diagnosing the failure of the image forming apparatus. That is, the above image information obtaining device corresponds to the failure information obtaining device of the system for diagnosing the failure of the present invention, and the above information controller corresponds to the information controller for controlling information for failure diagnosis. It is preferable that this system for diagnosing the failure is provided with a transmitting device for transmitting the chromatogram information to the information controller via the communications line. It is particularly preferable that the system for diagnosing the failure is provided with transmitting/receiving equipment such as a portable transmitting/receiving terminal. This portable transmitting/receiving terminal may be a failure information obtaining device.

The chromatography apparatus and the mobile phase applied to chromatography apparatus described above are also useful as a chromatography kit for analysis of the coloring material composition, and the chromatography apparatus and the mobile phase can constitute the kit of the present invention. It is particularly preferable that this kit is provided with the thin layer chromatography apparatus and the mobile phase containing ethanol. The thin layer chromatography apparatus may have the metallic oxide material layer formed on the surface of the sheet-shaped cellulosic material, and the mobile phase may be composed by only the ethanol. The thin layer chromatography apparatus may have a developing tank (chamber) for using the thin layer chromatography apparatus suitably.

The present invention will be described with reference to examples. However, the present invention is not limited to the following examples.

EXAMPLE 1

Examination of Separating Base Material

As the chromatography apparatus, two kinds of TLC plates A, B (A: Silica gel manufactured by MERCK, 60/Kieselguhr F254, 20×20 cm, aluminium sheet, B: cellulose F manufactured by MERCK, 20×20 cm, plastic sheet), a filter paper for paper chromatography (filter paper: 5C manufactured by ADVANTEC, 485×560 mm), and a sheet-shaped thin layer chromatography apparatus (chromato sheet (trade name) manufactured by Wako Pure Chemical Industries) of the present invention having a silica layer on the surface of a sheet-shaped cellulosic material were used, and two kinds of mobile phases easily handled were used. The thin layer chromatography was performed by using the equivalent mixture of inks of four colors (cyan, magenta, yellow, black, product number T038, T039, the coloring material is the dye) for ink jet printer Stylus C41, manufactured by Seiko Epson Corporation as the subject sample. Table 3 shows the compositions of the mobile phases and the results. As for the developing conditions, the size of each chromatography apparatus: 66 mm×100 mm, the spot amount of the subject sample: about 5 μL (artificial drying after spot), the developing time: 10 minutes, and the developing temperature: room temperature. The chromatogram was visually observed.

TABLE 3

| Chromatography | Composition of Mobile Phase | |
| --- | --- | --- |
| apparatus | Ethanol (100%) | Acetone:Methanol (3:2) |
| TLC Plate A | x | x |
| TLC Plate B | x | o |
| Filter Paper | x | x |
| Chromato Sheet | ◎ | ◎ |

As shown in Table 3, all the coloring materials contained in the subject sample were favorably separated in ethanol of 100% in the sheet-shaped thin layer chromatography apparatus of the present invention. However, the coloring materials were not separated at all in the other chromatography apparatuses. In an acetone-methanol mixture (3:2 (mixing ratio V/V %)), separation substantially equal to the case of ethanol was presented in the sheet-shaped thin layer chromatography apparatus of the present invention. In one kind of the TLC plate, the coloring materials were separated to some degree, and in the other chromatography apparatuses the coloring materials could not be separated. As described above, it was found that the chromatography apparatus of the present invention is particularly preferable for separating the coloring material composition as compared with the other thin layer chromatography apparatuses.

EXAMPLE 2

Examination 1 of Mobile Phase

The mobile phase suitable for the chromatography apparatus of the present invention used in Example 1 was examined. The mobile phases (seven kinds of A to G and fourteen kinds of a to n) of the various compositions shown in Table 4 as the mobile phase were prepared. As the subject sample, four colors (ink sets (product number T038, T039) of cyan (C), magenta (M), yellow (Y) and black (K)) for ink jet printer Stylus C41, manufactured by Seiko Epson Corporation, and six colors (ink sets (T0491, T0492, T0493, T0494, T0495, T0496) of (cyan (C), light cyan (LC), magenta (M), light magenta (LM), yellow (Y) and black (K)) for ink jet printer Stylus R210, manufactured by Seiko Epson Corporation were used. The chromatography was performed in the same developing conditions as Example 1 by setting the equivalent mixture of each color ink of the ink sets of four colors to a first group of the subject sample, and setting the equivalent mixture of each color ink of the ink sets of four colors and ink sets of six colors to a second group of the subject sample. Table 4 also shows the results.

TABLE 4

| | Composition of Mobile Phase | Degree of Separation* |
|---|---|---|
| A | Methanol | ○ |
| B | Ethanol | ◎ |
| C | Ethanol•Water (6:1) | ◎ |
| D | Acetone•Methanol (3:2) | ◎ |
| E | Acetone•Ethanol (1:1) | ◎ |
| F | Acetone•Ethanol•Methanol (2:2:1) | ◎ |
| G | Acetone•Methanol•THF•1,2-HD (20:10:1:1) | ○ |
| a | Water•Ethanol (1:4) | ○ |
| b | Methanol•Ethanol (1:4) | ◎ |
| c | Chloroform•Methanol (1:5) | ◎ |
| d | Water•Ethanol•2-propanol (1:4:4) | ◎ |
| e | THF•Methanol (1:1) | ○ |
| f | Hexane•Ethanol•Methanol (2:1:3) | ○ |
| g | Acetone | ○ |
| h | Acetone•TEG (20:1) | ○ |
| i | Acetone•2-Propanol (20:0.2) | ◎ |
| j | Acetone•Methanol•1,2-HD (20:10:1) | ◎ |
| k | Acetone•2-Propanol•1,2-HD (20:0.2:1) | ○ |
| l | Acetone•2-propanol•1,2-HD•Methanol (20:0.2:1:10) | ◎ |
| m | THF•water (10:1) | ○ |
| n | Chloroform | x |
| o | Xylene | x |
| p | Water | x |

THF: Tetrahydrofuran
1,2-HD: 1,2-hexanediol
TEG: Triethylene Glycol
*◎: separation of ingredients of three or more, ○: separation of ingredients of 1 to 2. x: separation impossibility As shown in Table 4, except for the mobile phases n, o, p, the coloring materials were also favorably separated by any mobile phase. Both the first group of the subject sample (the equivalent mixture of the ink for ink jet of CMYK) and the second group of subject sample (the equivalent mixture of the ink for ink jet of four colors of CMYK and in, for ink jet of six colors of CMYKLCLM) showed a favorable separation of the coloring materials in the mobile phases of A to G. When the chromatogram of the first group of the subject sample is contrasted with the second group, both can be clearly distinguished based on the color tone and position of the spot, and it could be visually recognized that the coloring materials of the first group of the subject sample are contained in the second group of the subject sample. Particularly, in B: ethanol 100%, C: ethanol.water (6:1), D: acetone.methanol (3:2), E: acetone.ethanol (1:1) and F: acetone-ethanol-methanol (2:2:1), three or more kinds of coloring materials were completely separated. Thereby, the first group and second group of the subject sample can be more easily distinguished, and it was confirmed that the coloring material composition of the first group of the subject sample was contained in the second group of the subject sample. FIG. 1 shows an example of the chromatogram when the mobile phase B (ethanol 100%) is used, and ink mixture of four colors and ink mixture of six colors are developed.

The same results were also observed in the mobile phases a to p. Particularly, a favorable separation was confirmed in b: methanol.ethanol (1:4), c: chloroform.methanol (1:5), d: water.ethanol.2-propanol (1:4:4), i: acetone.2-propanol (20: 0.2), j: acetone.methanol.1,2-hexanediol (20:10:1) and l: acetone-2-propanol.1,2-hexanediol.methanol (20:0.2:1:10).

In the case of the mobile phases (n, o, p) of only the nonpolar solvent and only water, the coloring materials could not be separated. As described above, it was found that the polar solvent compatible with water is preferably used as the mobile phase of the chromatography of the present invention.

EXAMPLE 3

Examination 2 of Mobile Phase

The solubility parameter of the mobile phase was examined. Referring to the various mobile phases shown in Table 5, the solubility parameters were calculated based on the formula (1) and Table 1. The chromatography was performed on the same developing conditions as Example 1 by using the chromatography apparatus of the present invention used in Example 1 as the Chromatography apparatus and using the equivalent mixture of the inks for ink jet (product number T038, T039, T0491, T0492, T0493, T0494, T0495, T0496)) manufactured by Seiko Epson Corporation, used in Example 2 as the subject sample. Table 5 and FIG. 2 show the results.

TABLE 5

| Kind | Composition of Mobile Phase | Solubility Parameter | Degree of Separation |
|---|---|---|---|
| A | Methanol | 14.5 | ○ |
| B | Ethanol | 12.7 | ◎ |
| C | Methanol•Ethanol (1:4) | 13.1 | ◎ |
| D | Ethanol•Water (6:1) | 14.2 | ◎ |
| E | Acetone•Methanol (3:2) | 11.7 | ◎ |
| F | Acetone•Ethanol (1:1) | 11.3 | ◎ |
| G | Acetone•Ethanol•Methanol (2:2:1) | 11.9 | ◎ |
| a | Water•Ethanol (1:4) | 14.8 | ○ |
| b | Chloroform•Methanol (1:5) | 13.6 | ◎ |
| c | THF•Methanol (1:1) | 11.8 | ○ |
| d | Hexane•Ethanol•Methanol (2:1:3) | 11.8 | ○ |
| e | Acetone | 9.9 | ○ |
| f | THF•Water (10:1) | 10.4 | ○ |
| g | Chloroform | 9.3 | x |
| h | Water | 23.4 | x |

Figure 2:
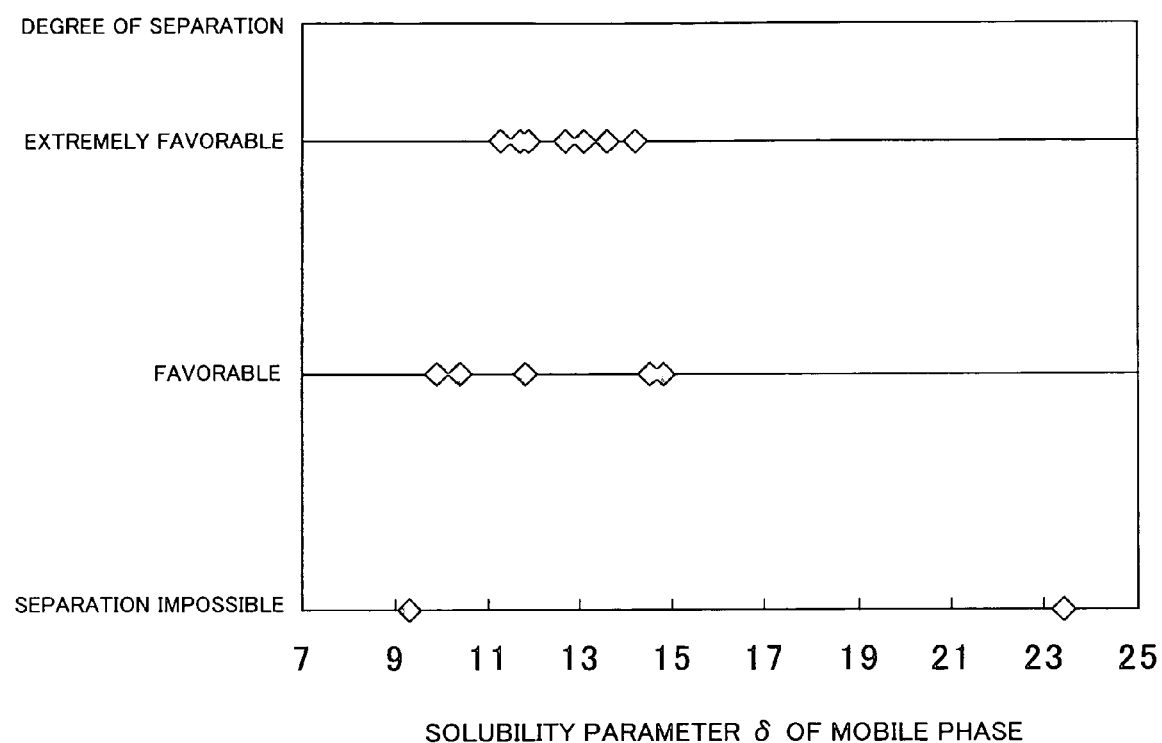
FIG. 2 shows the relationship between the solubility parameter of a mobile phase and the degree of separation of a spot.

As shown in Table 5 and FIG. 2, the solubility parameters of the mobile phases correspond to the separation performances of the coloring materials favorably, and the coloring materials can be separated at the solubility parameter of 9.5 to 16. Still better separation can be performed in the range of 11 to 14, and the best separation could be performed in the range of 12 to 14, particularly at about 13. As described above, it was found that the solubility parameter of the mobile phase is in a fixed range for the separation of the coloring materials. Therefore, it was found that the separation for various kinds of coloring materials can be controlled by using the solubility parameter. Particularly, referring to the dye of the ink for ink jet, the solubility parameter of the mobile phase was within the range of 9.5 to 16, preferably 11 to 15, more preferably 11 to 14. and still more preferably 12 to 14.

EXAMPLE 4

Examination of Water Content in Mobile Phase

The content of the water in the mobile phase of the mixture of ethanol-water was examined. The chromatography was performed for the same developing conditions as Example 1 by using the chromatography apparatus of the present invention used in Example 1 as the chromatography apparatus and using the equivalent mixture of the ink for ink jet (product number T038, T039, T0491, T0492, T0493, T0494, T0495, T0496)) manufactured by Seiko Epson Corporation, used in Example 2 as the subject sample. Table 6 also shows the composition and result of the mixture of ethanol.water.

TABLE 6

| Composition of Mobile Phase (Mixing Ratio V/V%) | | |
|---|---|---|
| Ethanol | Water | Degree of Separation |
| 100 | 0 | Extremely Favorable |
|  | 1 | Extremely Favorable |
|  | 2 | Extremely Favorable |
|  | 4 | Extremely Favorable |
|  | 5 | Extremely Favorable |
|  | 6 | Extremely Favorable to Considerably Favorable |
|  | 8 | Considerably Favorable |
|  | 10 | Considerably Favorable |
|  | 12 | Considerably Favorable |
|  | 17 | Considerably Favorable |

As shown in Table 6, it was found that a favorable separation of the coloring material is shown even if ethanol contains water of 17 v/v % to ethanol in the mobile phase. When ethanol contains water of 5 v/v % or less to ethanol, it was found that excellent separation capacity is shown as in the case of ethanol of 100% (no water).

The present invention claims benefit of priority to Japanese Patent Application No. 2004-363629 filed on Dec. 15, 2004, the contents of which are incorporated by reference herein in their entirety.

What is claimed is:

1. An analyzing method for coloring material composition, comprising a chromatography step of loading a subject sample containing the coloring material composition to a chromatography apparatus that holds a separating base material containing a cellulosic material and a metallic oxide material, so as to separate analytes in the coloring material composition using a mobile phase of a liquid, wherein the mobile phase has a solubility parameter represented by the following formula (1) that is within the range of 9.5 to 16:

$$\text{Solubility Parameter of Mobile Phase } (d) = \sum_{i=1\,ton} (di \times Ri), \quad \text{Formula (1)}$$

wherein i is one or more integers; di is the solubility parameter of the i-th solvent of n kinds of solvents constituting the mobile phase; Ri is the mixing ratio in the mobile phase of the i-th solvent of n kinds of solvents constituting the mobile phase; and the total from $R_1$ to $R_n$ is 1.

2. The analyzing method according to claim 1, wherein the separating base material has a silica material and/or alumina material layer formed on the surface of the cellulosic material.

3. The analyzing method according to claim 2, wherein the chromatography apparatus is a thin layer chromatography apparatus, and the separating base material has the silica material layer formed on the surface of the cellulosic material layer.

4. The analyzing method according to claim 1, wherein the mobile phase is mainly composed of a polar solvent compatible with water.

5. The analyzing method according to claim 1, wherein the mobile phase is mainly composed of ethanol.

6. The analyzing method according to claim 1, wherein the subject sample is either of an extracted matter from an image forming apparatus containing the coloring material composition and an extracted matter from an image part formed on a recorded matter containing the coloring material composition.

7. The analyzing method according to claim 1, further comprising an identification step of identifying the coloring material composition contained in the subject sample based on the separating data of one kind or two kinds or more of coloring materials contained in the subject sample obtained by the chromatography step, and the separating data of the coloring material composition for analysis.

8. The analyzing method according to claim 1, wherein the coloring material composition is an ink composition for ink jet.

9. A chromatography kit for analyzing a coloring material composition, comprising:
a thin layer chromatography apparatus that holds a separating base material containing a cellulosic material and a metallic oxide material; and
a mobile phase applied to the thin layer chromatography apparatus containing ethanol, said mobile phase having a solubility parameter represented by the following formula (1) that is within the range of 9.5 to 16:

$$\text{Solubility Parameter of Mobile Phase } (d) = \sum_{i=1\,ton} (di \times Ri), \quad \text{Formula (1)}$$

wherein i is one or more integers; di is the solubility parameter of the i-th solvent of n kinds of solvents constituting the mobile phase; Ri is the mixing ratio in the mobile phase of the i-th solvent of n kinds of solvents constituting the mobile phase; and the total from $R_1$ to $R_n$ is 1.

* * * * *